United States Patent [19]

Moreschini

[11] Patent Number: 5,048,731
[45] Date of Patent: Sep. 17, 1991

[54] EASY LOAD—GET IT ALL DENTAL PROPHYLACTIC POLISHING PASTE CONTAINER DISPENSER WITH INTEGRAL RING LIKE HOLDING DEVICE

[76] Inventor: Ronald Moreschini, 2929 7th Ave., Pueblo, Colo. 81008

[21] Appl. No.: 439,107

[22] Filed: Nov. 20, 1989

[51] Int. Cl.$^5$ ................. B65D 47/10; A61C 3/00
[52] U.S. Cl. ................................ 222/541; 433/163
[58] Field of Search ................ 433/163, 141, 80, 25, 433/229; 222/192, 541

[56] References Cited

U.S. PATENT DOCUMENTS

| | | | |
|---|---|---|---|
| 2,222,741 | 11/1940 | Bush | 433/163 |
| 2,665,479 | 1/1954 | Weldon | 433/163 |
| 3,327,391 | 6/1967 | Malm | 433/163 |
| 4,717,057 | 1/1988 | Porteus | 433/163 X |

OTHER PUBLICATIONS

Kent Dental Catalog, Spring/Summer 1984, pp. 171-172.
Nupro brochure from Janar Co., Inc.

*Primary Examiner*—Andres Kashnikow
*Assistant Examiner*—Lesley D. Morris
*Attorney, Agent, or Firm*—John W. Huckert

[57] ABSTRACT

The present invention is a dental prophylactic polishing paste container-dispenser of unique design, shape and size having an integral ring like holding device as part of the body member to be unfolded or pulled down and used to secure the container-dispenser to the hand of the operator by slipping the ring like device over one of the fingers where it will be held securely by the memory of the plastic ring like device trying to return to its original position. The present invention is designed to allow the prophy cup to be inserted easily and fully able to reach all the internal surfaces of the container-dispenser. The present invention has sloping sides that angle downward and inward at about forty degrees to meet a smallish bottom surface area that is only slightly larger in diameter than the diameter of the open end of the prophy cup allowing the operator to push any remaining polishing paste down the sloping side of the container-dispenser to the smallish bottom area trapping the polishing paste in the open end of the prophy cup. The present invention will contain and dispense sterile individual portions of polishing paste with an infinite variety as to flavor, color, grit, medicaments and eliminate cross contamination while being easy to manufacture and use, saving materials, time, effort, frustration and money.

18 Claims, 1 Drawing Sheet

U.S. Patent
Sep. 17, 1991
5,048,731
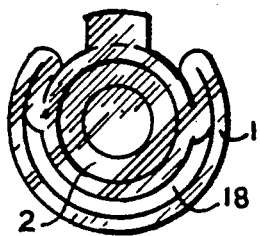
Fig. 1.
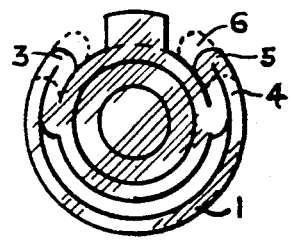
Fig. 2.
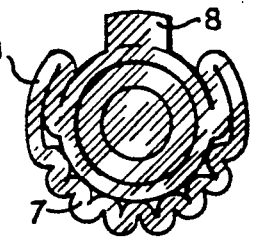
Fig. 3.
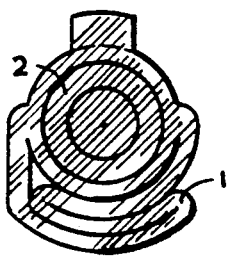
Fig. 5.
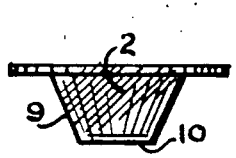
Fig. 4.
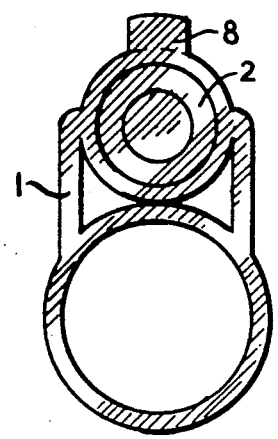
Fig. 6.
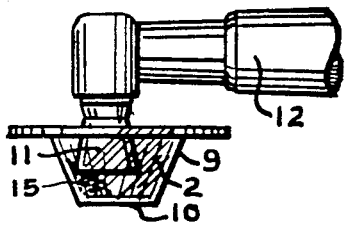
Fig. 7.
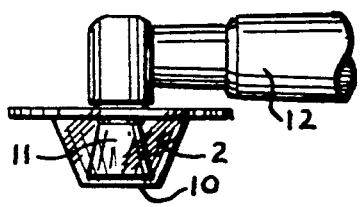
Fig. 8.
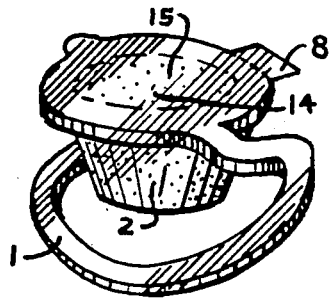
Fig. 9
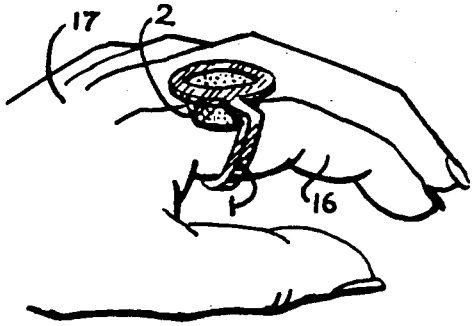
Fig. 10.
Fig. 11.

EASY LOAD—GET IT ALL DENTAL PROPHYLACTIC POLISHING PASTE CONTAINER DISPENSER WITH INTEGRAL RING LIKE HOLDING DEVICE

This invention relates generally to devices used in the dental profession and more specifically to devices used in dental prophylaxis.

As part of a dental prophylaxis the teeth are polished by a prophylactic polishing paste that is applied to the teeth by the use of a small rubber cup commonly called a prophy cup. The prophy cup is filled or loaded with the prophylactic polishing paste from an individual sized container-dispenser and then held against the surface of the tooth while being mechanically rotated, this in turn forces the polishing paste to abrade across the surface of the tooth polishing it.

A common problem with known devices of conventional type is the difficulty in loading, or filling the prophy cup with the prophylactic polishing paste, especially when most of the polishing paste has been removed from the container-dispenser. Another common problem with known devices is the difficulty in holding the container-dispenser with the left hand while also holding the patients lip out of the way of the rotating prophy cup while engaged with the task of performing a dental prophylaxis.

This invention, an uniquely designed dental prophylactic polishing paste container dispenser having a shape and size of such dimensions, and a ring like holding device that is part of the container-dispenser and will unfold and slide over the finger of the operators left hand and there be held securely by the spring like action of the ring like device trying to return to its original position. The size and shape of this device is such that the depth of the container-dispenser is less than the length of the prophy cup allowing the prophy cup to be thrust straight down all the way to the bottom surface of the container-dispenser. Since the bottom surface of the container-dispenser is only slightly larger in diameter than the diameter of the open end of the prophy cup any portion of polishing paste left in the container-dispenser can be pushed down along the sloping sides of the container-dispenser to be trapped and forced into the open end of the prophy cup eliminating waste and saving the operator time and frustration. The unique design of this container-dispenser could be mass produced in a plastic material using the die cut method, filled with a sterile polishing paste of infinite variety as to grit (fine, medium or course), flavor (mint, cherry), medicaments (fluoride, etc.), and then sealed with a removable peel away top at a very low cost. This would save money, waste, time, effort, frustration, and eliminate cross contamination.

An object of the present invention is to provide a prophylactic polishing paste container-dispenser that will save money, time, effort, frustration and materials.

Another object of the present invention is to provide a prophylactic polishing paste container-dispenser that will eliminate waste by allowing the polishing paste to be removed.

Another object of the present invention is to provide a prophylactic polishing paste container-dispenser that will allow the operator to load, or fill, the prophy cup with the polishing paste quickly, saving time.

Another object of the present invention is to provide a prophylactic polishing paste container-dispenser that will allow the operator to load, or fill, the prophy cup with the polishing paste easily, saving effort.

Another object of the present invention is to provide a prophylactic polishing paste container-dispenser that will allow the prophy cup to be pushed straight down to the bottom of the container-dispenser allowing the open end of the prophy cup to fully contact the bottom surface forcing the polishing paste into the prophy cup.

Another object of the present invention is to provide a prophylactic polishing paste container-dispenser with sloping sides ending in a bottom surface only slightly larger in diameter than the diameter of the open end of the prophy cup. This will allow the operator to push any remaining paste down the sloping side to be trapped and forced into the open end of the prophy cup.

Another object of the present invention is to provide a prophylactic polishing paste container-dispenser that will hold sterile portions of prophylactic polishing paste.

Another object of the present invention is to provide a prophylactic polishing paste container-dispenser that will hold individual sized portions of prophylactic polishing paste.

Another object of the present invention is to provide a prophylactic polishing paste container-dispenser that would hold different grit size polishing paste (fine, medium, course).

Another object of the present invention is to provide a prophylactic polishing paste container-dispenser that would hold different flavored polishing paste (mint, cherry etc.).

Another object of the present invention is to provide a prophylactic polishing paste container-dispenser that has a built in ring like device that unfolds and opens to fit over the finger of the operator holding the container-dispenser securely to the finger of the operator.

Another object of the present invention is to provide a prophylactic polishing paste container-dispenser that has a built in ring like device availabe in different sizes (small, medium or large).

Another object of the present invention is to provide a prophylactic polishing paste container-dispenser that has a built in ring like device that due to its unique spring like expandible shape will fit any size finger the operator might have.

Another object of the present invention is to provide a prophylactic polishing paste container-dispenser that has a unique built in, fold down ring like device that will hold the container-dispenser firmly and securely to the finger of the operator due to the memory of the plastic ring like device trying to return to its original unfolded position.

Another object of the present invention is to provide a prophylactic polishing paste container-dispenser that is simple in design, easy to produce, low in cost and convenient to use.

These and other objects and advantages of this invention will become apparent upon reading the following description of which the attached drawings form a part.

FIG. 1. Is a top view of the present invention with the folded ring like device.

FIG. 2. Is a top view of the present invention showing how the ring like device can be made longer or shorter.

FIG. 3. Is a top view of the present invention showing the ring like device with an expandable spring like portion.

FIG. 4. Is a side view of the present invention showing the sloping sides and small bottom area.

FIG. 5. Is a top view of the present invention with the ring like device made in another configuration.

FIG. 6. Is a top view of the present invention with the ring like device in another of many possible configurations.

FIG. 7. Is a side view of the present invention showing how the prophy cup can push any remaining polishing paste down the sloping side to be forced into the open end of the prophy cup by the close fitting bottom surface.

FIG. 8. Is a side view of the present invention showing how the prophy cup fits into the small bottom surface of the container-dispenser.

FIG. 9. Is a perspective view of the present invention showing the built in ring like device pulled down slightly.

FIG. 10. Is a perspective view of the present invention showing the built in ring like device fully extended and ready to be slipped over the finger of the operator. It also shows the top cover and seal of the container-dispenser partially lifted away.

FIG. 11. Is a perspective view of the operators hand showing how the ring like device holds the container-dispenser to the operators finger.

Refering to the drawing;

In FIG. 1. it is seen how the folded up, built in ring like device 1, is made from the contiguous lip like portion 18, of the plastic prophylactic polishing paste container-dispenser 2.

In FIG. 2. we can see how the built in ring like device 1, can have a longer or shorter back portion 3, which can make the size of the ring like device small, 4, medium, 5, or large, 6, In FIG. 3. we see how the built in ring like device 1, can have a zig-zag shape 7, that can expand and spring back allowing the ring like device to fit any size finger. We also see the top cover lifting tab 8.

In FIG. 4. we see the sloping sides 9, and the small flat bottom surface 10, of the container-dispenser.

In FIG. 5. we see the ring like device 1, in a different configuration.

In FIG. 6. we see the ring like device 1, in another of many possible configurations. This configuration shows the ring like device unfolded in the same plane as the flat flange and flush with the top thereof.

In FIG. 7. we see how the prophy cup 11, here shown attached to a prophy angle 12, can push any polishing paste 15, left in the container-dispenser 2, down the sloping side 9, trapping the polishing paste 15, at the bottom surface 10, where it will be forced into the open end of the prophy cup 11.

In FIG. 8. the prophy cup 11, is flush against the bottom surface 10, of the container-dispenser 2. Notice the container-dispenser is short enough to allow the prophy cup 11, to reach the bottom surface 10, with out any interference with the prophy angle 12.

In FIG. 9. we see a perspective view of the present invention showing the ring like device 1, pulled down a short distance from its original position which was flush with the top of the container-dispenser 2,. We also see the sealed top 14, in its original position protecting the sterile prophylactic polishing paste 15, inside the container-dispenser 2.

In FIG. 10. we see a perspective view of the present invention showing the ring like device 1, fully extended and ready to be slipped over the finger 16, of the operators hand 17. We also see the peel away top 14, partially removed from the container-dispenser 2, exposing the sterile polishing paste 15.

In FIG. 11. We see a perspective view of the operators hand 17, showing the container-dispenser 2, secured to the finger 16, by the ring like device 1. where it is held by the spring like action of the ring like device 1, trying to return to its original position.

This invention may be further developed within the scope of the following attached claims, accordingly, it is desired that the fore going description be read merely as being illustrative of an operative embodiment of this invention and not in a strictly limiting sense.

What is claimed is:

1. A dental prophylactic polishing paste container-dispenser for use with a prophy cup and polishing paste comprising: a conically shaped body member of plastic, the larger end of said body member having a central opening surrounded by a contiguous flat flange, said body member of such a shape and size to allow said prophy cup easy access for complete removal of all the polishing paste contained therein and having a ring like device as an integral part of said flange, and said ring like device being of a folded type which as unfolded is in the same plane as said flat flange and flush with the top thereof.

2. A container-dispenser as set forth in claim 1, wherein said container-dispenser has a depth of the central opening that is less than the length of the prophy cup.

3. A container-dispenser as set forth in claim 1, wherein said container-dispenser has sides sloping downward and inward at about a fourty degree angle.

4. A container-dispenser as set forth in claim 1, wherein said container-dispenser has a bottom surface diameter only slightly larger than the diameter of the prophy cup at the prophy cups lower open end.

5. A container-dispenser as set forth in claim 1, wherein said container-dispenser has a central opening of such diameter to hold enough polishing paste to complete the average dental prophylactic procedure.

6. A container-dispenser as set forth in claim 1, wherein said container-dispenser is of such size and shape to allow the prophy cup to contact the sides and the bottom surface with the prophy cups open end without interference of the prophy angle touching the container-dispenser in any manner.

7. A container-dispenser as set forth in claim 1, wherein said container-dispenser would be filled with a polishing paste of different grits, (fine, medium or course).

8. A container-dispenser as set forth in claim 1, wherein said container-dispenser would be filled with a polishing paste of different flavors, (mint, cherry, etc.).

9. A container-dispenser as set forth in claim 1, wherein said container-dispenser would be filled with a polishing paste of different colors.

10. A container-dispenser as set forth in claim 1, wherein said container dispenser would be filled with a polishing paste containing different medicaments, (fluoride, etc.).

11. A container-dispenser as set forth in claim 1, wherein said container-dispenser would be filled with individual portions of polishing paste.

12. A container-dispenser as set forth in claim 1, wherein said container-dispenser would be filled with sterile individual sized portions of polishing paste.

13. A container-dispenser as set forth in claim 1, wherein said container-dispenser has a sealed peel away top cover.

14. A dental prophylactic polishing paste container-dispenser for use with a prophy cup and polishing paste comprising: a conically shaped body member, the larger end of said body member having a central opening surrounded by a flange, said body member of such a shape and size to allow said prophy cup easy access for complete removal of all the polishing paste contained therein and having a ring like device as an integral part of said flange, wherein said container-dispenser is available with different size ring like devices, (small, medium or large), as an integral part of it.

15. A container-dispenser as set forth in claim 14, wherein said container-dispenser has a sealed peel away top cover.

16. A dental prophylactic polishing paste container-dispenser for use with a prophy cup and polishing paste comprising: a conically shaped body member, the larger end of said body member having a central opening surrounded by a flange, said body member of such a shape and size to allow said prophy cup easy access for complete removal of all the polishing paste contained therein and having a folded ring like device as an integral part of said flange, wherein said folded ring like device is provided with an expandable spring like section in the ring like device so one size can fit any size finger, wherein said expandable spring like section comprises a portion of said ring in zig-zag shape that can expand and spring back.

17. A container-dispenser as set forth in claim 16, wherein said container-dispenser has a sealed peel away top cover.

18. A container-dispenser as set forth in claim 17, wherein said peel away top cover has a lifting tab.

* * * * *